US011624084B2

(12) United States Patent
Teng et al.

(10) Patent No.: US 11,624,084 B2
(45) Date of Patent: Apr. 11, 2023

(54) OFF-TARGET CAPTURE REDUCTION IN SEQUENCING TECHNIQUES

(71) Applicant: ILLUMINA, INC., San Diego, CA (US)

(72) Inventors: Li Teng, San Diego, CA (US); Chia-Ling Hsieh, San Diego, CA (US); Charles Lin, San Diego, CA (US); Han-Yu Chuang, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 306 days.

(21) Appl. No.: 16/782,833

(22) Filed: Feb. 5, 2020

(65) Prior Publication Data

US 2020/0172960 A1    Jun. 4, 2020

Related U.S. Application Data

(62) Division of application No. 15/286,374, filed on Oct. 5, 2016, now Pat. No. 10,577,643.

(60) Provisional application No. 62/238,411, filed on Oct. 7, 2015.

(51) Int. Cl.
*C12Q 1/6806*    (2018.01)

(52) U.S. Cl.
CPC ................... *C12Q 1/6806* (2013.01)

(58) Field of Classification Search
CPC ............... C12Q 2535/122; C12Q 2537/159
See application file for complete search history.

(56) References Cited

U.S. PATENT DOCUMENTS

| 6,632,655 B1 | 10/2003 | Mehta et al. | |
|---|---|---|---|
| 2001/0053519 A1 | 12/2001 | Fodor et al. | |
| 2003/0008807 A1 | 1/2003 | Levine et al. | |
| 2003/0148288 A1* | 8/2003 | Tang .................... | C12Q 1/6844 435/6.16 |
| 2003/0175701 A1 | 9/2003 | Griffiths et al. | |
| 2003/0175709 A1 | 9/2003 | Murphy et al. | |
| 2005/0003369 A1 | 1/2005 | Christians et al. | |
| 2005/0095582 A1 | 5/2005 | Gillim-Ross et al. | |
| 2005/0273274 A1 | 12/2005 | Evans et al. | |
| 2006/0281108 A1 | 12/2006 | Monforte et al. | |
| 2009/0155784 A1 | 6/2009 | O'Toole et al. | |
| 2010/0029498 A1 | 2/2010 | Gnirke et al. | |
| 2010/0076185 A1 | 3/2010 | Adey et al. | |
| 2010/0190265 A1 | 7/2010 | Dufva et al. | |
| 2010/0331204 A1* | 12/2010 | Jeddeloh .............. | C12Q 1/6809 536/23.6 |
| 2011/0091939 A1* | 4/2011 | Cui ........................ | C07H 21/04 252/60 |
| 2011/0177263 A1 | 7/2011 | Hasegawa et al. | |
| 2012/0094353 A1 | 4/2012 | Baelum et al. | |
| 2014/0031240 A1 | 1/2014 | Behlke et al. | |
| 2014/0120522 A1 | 5/2014 | Chou et al. | |
| 2014/0127792 A1 | 5/2014 | Kain et al. | |
| 2014/0287468 A1 | 9/2014 | Richard et al. | |
| 2015/0111769 A1* | 4/2015 | Suehiro ................ | C12Q 1/6886 435/6.12 |
| 2015/0275267 A1 | 10/2015 | O'Neil et al. | |
| 2016/0046998 A1 | 2/2016 | Verrant et al. | |
| 2016/0068889 A1 | 3/2016 | Gole et al. | |
| 2017/0188553 A1 | 7/2017 | Shen | |

FOREIGN PATENT DOCUMENTS

| CN | 104004854 A | 8/2014 |
|---|---|---|
| JP | 2009207418 A | 9/2009 |
| JP | 2010136657 A | 6/2010 |
| JP | 2014018127 A | 2/2014 |
| WO | 2010091870 A1 | 8/2010 |

OTHER PUBLICATIONS

Chakrabarty et al. ZooKeys 346:29-41 (Year: 2013).*
Guo et al. BMC Genomics 13: 194 (Year: 2012).*
Rajalahti et al.Eur. Respir J. 23:446-451 (Year: 2004).*
Albert et al., Direct selection of human genomic loci by microarray hybridization. Nature Methods 4 (11): 903-905 (Year: 2007).
Altschul SF, Gish W, Miller W, Myers EW and Lipman DJ. Basic local alignment search tool. J. Mol. Biol. 1990. 215: 403-410.
Bao et al., Automated De Novo Identification of Repeat Sequence Families in Sequenced Genomes. Genome Research 12:1269-1276 (Year: 2002).
Benson, G., Tandem repeats finder: a program to analyze DNA sequences. Nucleic Acids Research 27(2): 573-580 (Year: 1999).
Blumenstiel, Brendan, et al: "Targeted Exon Sequencing by in-Solution Hybrid Selection", Current Protocols in Human Genetics, John Wiley & Sons, Inc, US, Jul. 1, 2010 (Jul. 1, 2010), pp. 18.4.1-18.4.24, XP002714375.
Cottrell et al., Validation of a Next-Generation Sequencing Assay for Clinical Molecular Oncology. J. of Molecular Diagnostics 16(1): 89-105 (Jan. 2014).
De Koning et al., Repetitive Elements May Comprise Over Two-Thirds of the Human Genome. Plos Genetics 7(12): e1002384 (Year: 2011).
Doggett, NA., Overview of Human Repetitive DNA Sequences. Current Protocols in Human Genetics A.1.B1-A.1.B.5 (Year: 2000).
Eden et al., Discovering Motifs in Ranked Lists of DNA Sequences. Plos Computational Biology 3(3): e39 (Year: 2007).
Edgar et al., PILER: identification and classification of genomic repeats. Bioinformatics 21 (Suppl. 1): i152-i158 (Year: 2005).

(Continued)

*Primary Examiner* — Ethan C Whisenant

(74) *Attorney, Agent, or Firm* — Fletcher Yoder P.C.

(57) ABSTRACT

Presented herein are methods and compositions for enhancing specific enrichment of target sequences in a nucleic acid library. Off-target hybridization probes may be used to reduce binding and/or capture of off-target regions of a nucleic acid library in a targeted sequencing workflow. The off-target hybridization probes may be specific for locations known to generate off-target sequencing reads for a particular set of hybridization probes.

12 Claims, 14 Drawing Sheets

(56) References Cited

OTHER PUBLICATIONS

Feng J, Liu T, Qin B, Zhang Y, Liu XS. Identifying ChIP-seq enrichment using MACS. Nat Protoc. 2012. 7(9): 1728-40.
Gnirke et al., Solution hybrid selection with ultra-long oligonucleotides for massively parallel targeted sequencing. Nature Biotechnology 27(2): 182-189 (Year: 2009).
Gu et al., Identification of repeat structure in large genomes using repeat probability clouds. Analytical Biochemistry 380: 77-83 (Year: 2008).
Guo Y, Mahony S and Gifford DK. High Resolution Genome Wide Binding Event Finding and Motif Discovery Reveals Transcription Factor Spatial Binding Constraints. PLoS Computational Biology 2012: 8(8): e1002638.
Harismendy et al., Evaluation of next generation sequencing platforms for population targeted sequencing studies. Genome Biology 10: R32 (Year 2009).
Hodges, Emily et al: "Genome-wide in situ exon capture for selective resequencing", Nature Genetics, Nature Publishing Group, US, vol. 39, No. 12, Dec. 1, 2007 (Dec. 1, 2007), pp. 1522-1527, XP002524508.
Jurka et al., CENSOR. Computer Chem. 20(1): 119-121 (Year: 1996).
Jurka et al., Repbase Update. Trends in Genetics 16(9): 418 (Year: 2000).
Karlin et al., Methods for assessing the statistical significance of molecular sequencing features by using general scoring schemes. PNAS 87: 2264 (Year: 1990).
Kim et al., A proposed metric for assessing the measurement quality of individual microarrays. BMC Bioinformatics 7: 35 (Year: 2006).
Maeda et al., Molecular Biology and Evolution 5(1): 1-20 (Year: 1988).
Mamanova, Lira, et al: "Target-enrichment strategies for next-generation sequencing", Nature Methods, Nature Publishing Group, GB, vol. 7, No. 2, Feb. 1, 2010 (Fev. 1, 2010), pp. 111-118, XP002658413.
Price et al., De novo identification of repeat families in large genomes. Bioinformatics 21 (Suppl. 1): i351-1358 (Year: 2005).
Qin et al., Empirical evaluation of data transformations and ranking statistics for microarray analysis. Nucleic Acids Research 32(18): 5471-5479 (Year: 2004).
Rigaill GJ, Cadot S, Kluin RJC, Xue Z, Bernards R, Majewski IJ et al . . . A regression model for estimating DNA copy number applied to capture sequencing data. Bioinformatics. 2012;28:2357-65.
Tanner et al., J. of Molecular Diagnostics vol. 16, No. 3 (Year: 2014).
The ENCODE Project Consortium. The ENCODE (ENCyclopedia of DNA Elements) Project. Science. 2004. 306 (5696): 636-40.
Wilbanks EG and Faccitti MT. Evaluation of Algorithm Performance in ChIP-seq peak detection. PloS One. 2010. 8: 5 (7): e11471.
Japanese Office Action for Application No. JP2018-517837, dated Apr. 16, 2019, 7 pgs.
PCT International Search Report & Written Opinion for PCT Application No. PCT/US2016/055736 dated Feb. 2, 2017; 42 Pages.
Kuilman, T. , et al., "CopywriteR: DNA copy number detection from off-target sequence data", Genome Biology 16(49), Feb. 27, 2015, 1-15.
Zheng, M. , et al., "Window of Life: An Overview of the Frontiers of Life Sciences", The Fourth Military Medical University Press, Jun. 30, 2014, 27-29 with english translation.
CN Application No. 201680068374.4 Office Action, dated Mar. 11, 2021.
Extended European Search Report and Written Opinion for EP Application No. 21188310.3 dated Dec. 21, 2021, 8 pgs.

\* cited by examiner

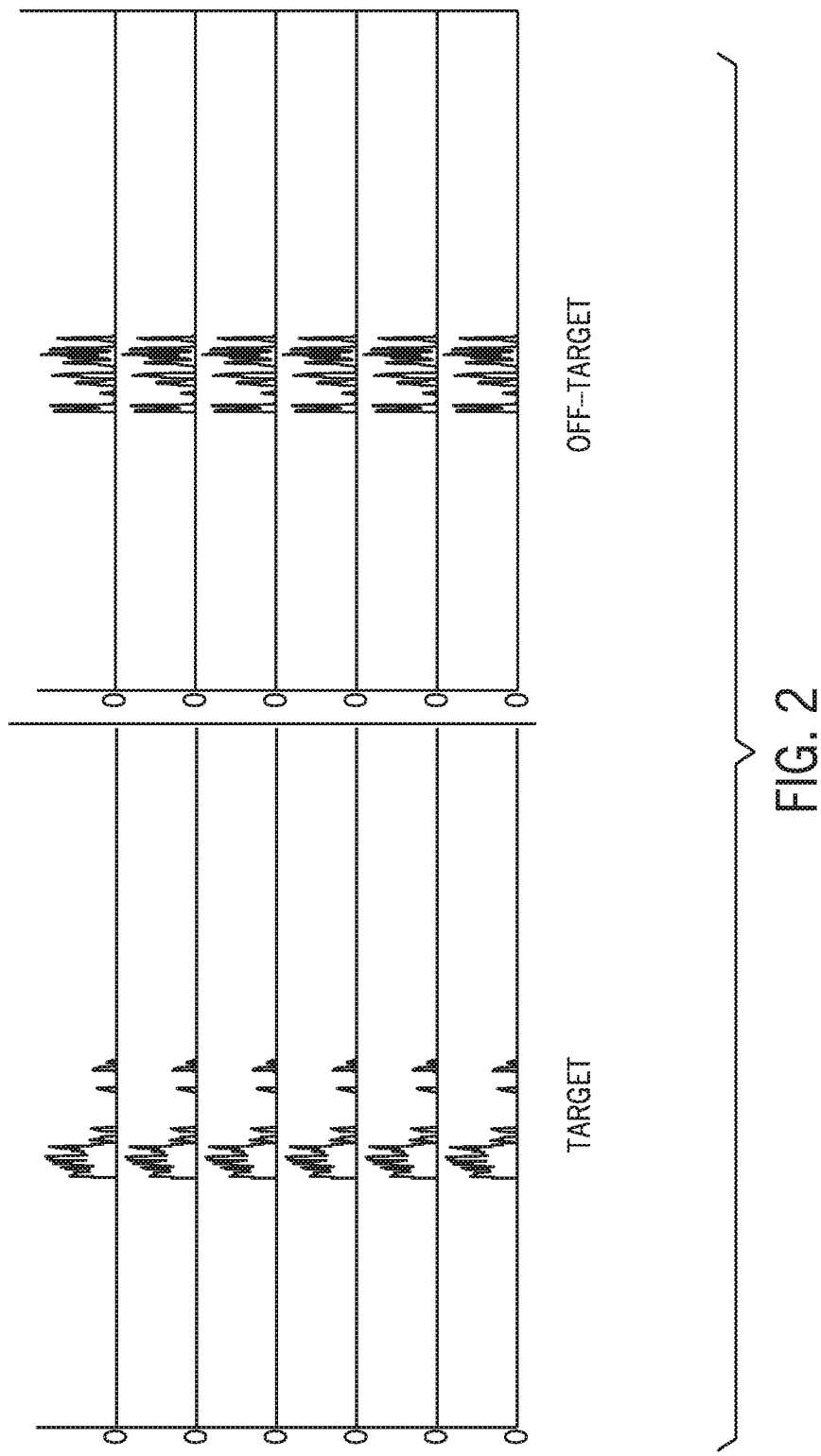

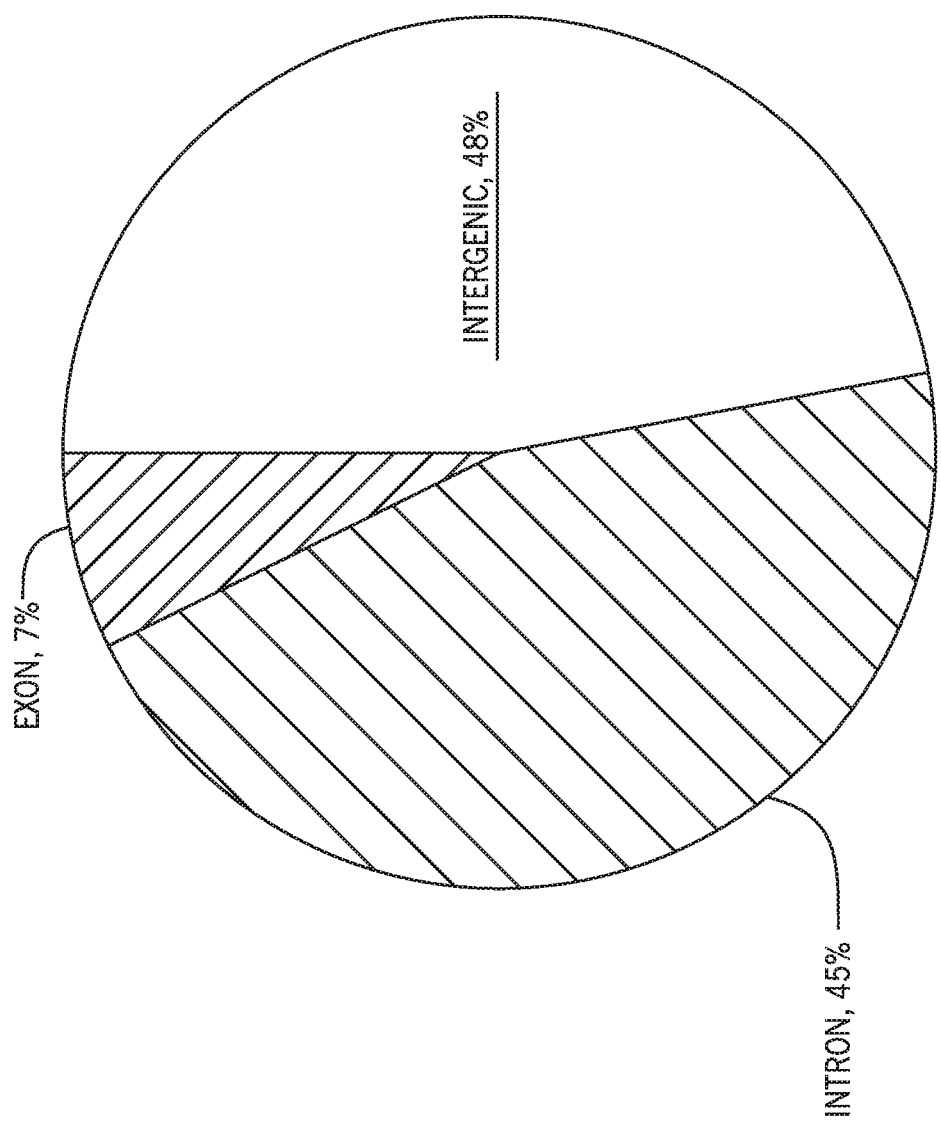

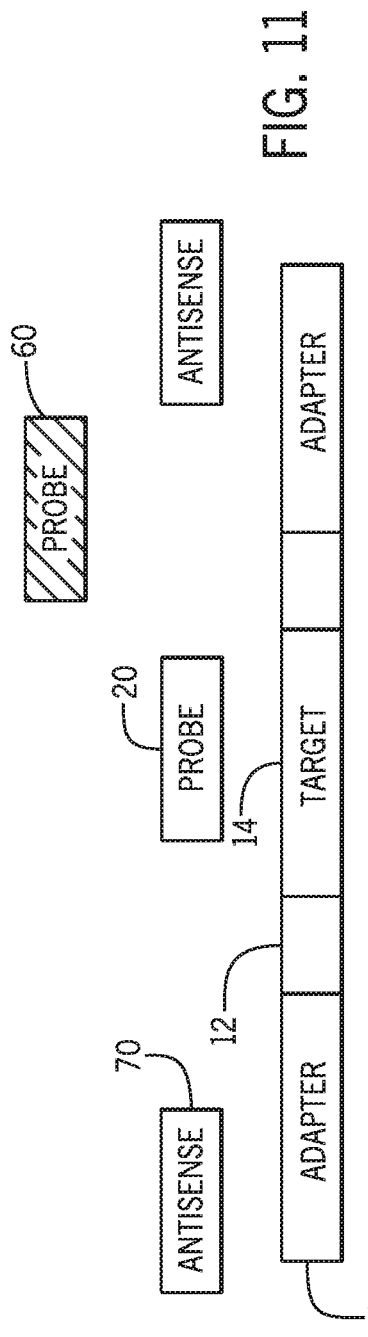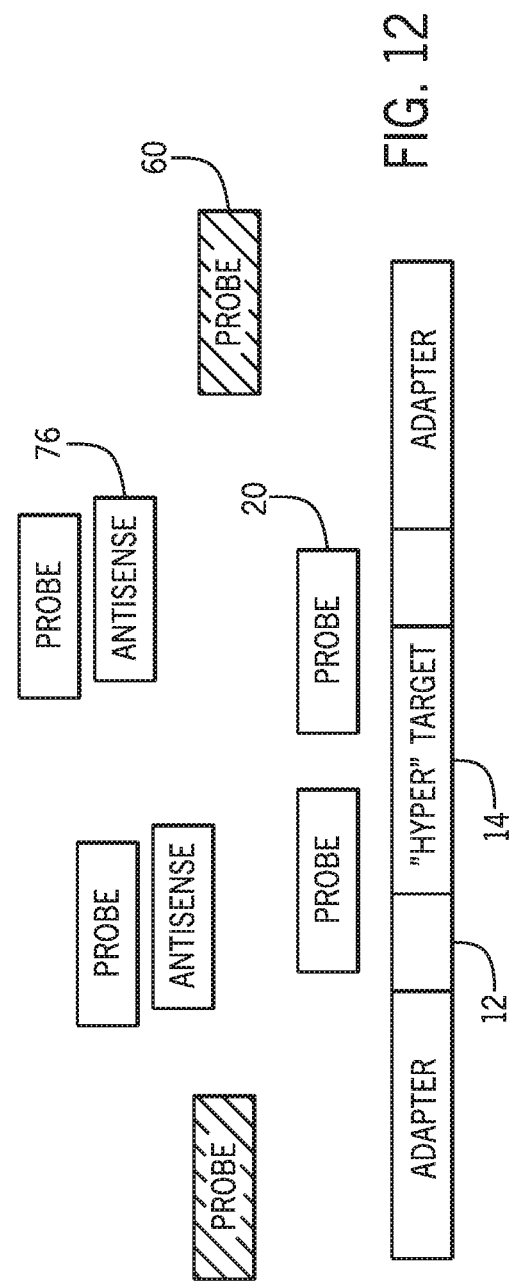

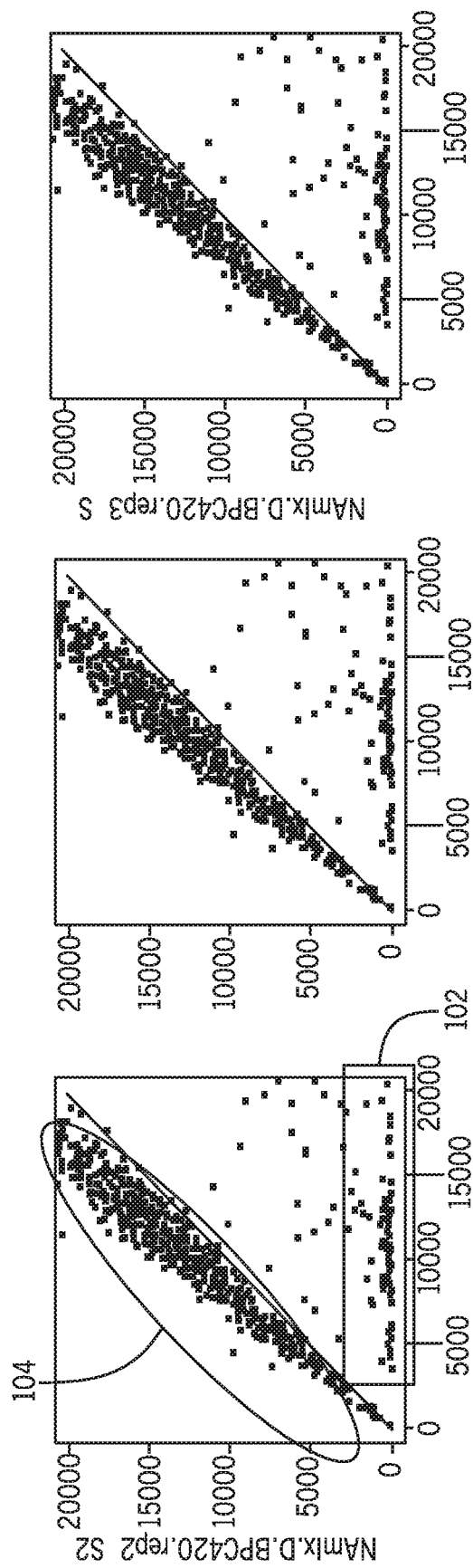

OFF-TARGET CAPTURE REDUCTION IN SEQUENCING TECHNIQUES

CROSS REFERENCE TO RELATED APPLICATIONS

The present application is a divisional of U.S. patent application Ser. No. 15/286,374, entitled "OFF-TARGET CAPTURE REDUCTION IN SEQUENCING TECHNIQUES," filed on Oct. 5, 2016, which claims priority to U.S. Provisional Application No. 62/238,411, entitled "DATA-GUIDED DESIGN OF HYBRID CAPTURE OFF-TARGET REDUCERS" and filed Oct. 7, 2015, the disclosures of which are incorporated herein by reference for all purposes.

BACKGROUND

The present disclosure relates generally to the field of nucleic acid sequencing techniques. More particularly, the disclosure relates to techniques for enriching target capture and reducing off-target capture of nucleic acids to be sequenced in a targeted sequencing workflow.

Sequencing methodology of next-generation sequencing (NGS) platforms typically makes use of nucleic acid fragment libraries. In targeted sequencing techniques, a subset of fragments containing genes or regions of interest of the genome are isolated from the nucleic acid library and sequenced. Targeted approaches using NGS allow researchers to focus time, expenses, and data analysis on specific areas of interest. Such targeted analysis can include the exome (the protein-coding portion of the genome), specific genes of interest (custom content), targets within genes, or mitochondrial DNA. Targeted approaches contrast with whole genome sequencing approaches that are more comprehensive, but that also involve sequencing regions of the genome that may not be of interest to all users.

In one example of a targeted sequencing technique, hybrid capture methods use a panel or set of probes that hybridize to target sequences in the nucleic acid library. Hybridization of the probes to the target sequences allows these sequences to be separated from the rest of the fragments in the library for sequencing. By targeting only a portion of the nucleic acid library, hybrid capture methods avoid sequencing of off-target nucleic acid fragments that do not contain sequences of interest. However, unlike amplicon-based target enrichment methods, hybrid capture methods have a higher rate of off-target sequencing and, in turn, lower on-target specificity. For example, certain hybrid capture methods generally achieve only 40%~60% efficiency, despite the use of commercial hybridization blockers such as Cot1, tRNA, salmon sperm DNA, poly(dIdC) and blockers targeting the universal adapters of library fragments. The off-target reads not only waste sequencing yield, but also potentially compromise variant calling for somatic mutations of low frequency. Therefore, there is a need for improved enrichment methods that provide for higher specificity in targeted sequencing techniques.

BRIEF SUMMARY

Presented herein are techniques for enrichment of target sequences in a nucleic acid library and reducing the capture of off-target sequences by a set of target hybridization probes. Because target hybridization probes have imperfect specificity for their nucleic acid targets, a sequencing run using a set of target hybridization probes may also include a certain percentage of reads that represent sequences that are off-target. For example, in an exome sequencing reaction, certain hybridization probes may pull down intronic or intergenic sequences from a nucleic acid library along with target sequences. These off-target fragments, once pulled down, are then present in the pool of nucleic acid fragments that are sequenced. While the sequencing information representative of the off-target reads is typically discarded, the present techniques use acquired sequencing information of these off-target reads to design hybridization probes that are specific for the off-target sequences and that are used to separate and/or remove fragments that include these sequences from the pool of fragments captured by the target-specific hybridization probes. The off-target hybridization probes are designed based on analysis of the off-target reads of a hybrid capture sequencing run that is performed with a set of target hybridization probes. In certain embodiments, the on-target probe design may also be based on systematic off-target analysis across samples to improve the specificity of the target hybridization probes for their desired targets.

Presented herein is a method of reducing off-target capture in a targeted sequencing reaction. The method includes the steps of providing a set of off-target hybridization probes that specifically bind to a plurality of off-target sequences present in a nucleic acid library generated from a sample, the nucleic acid library comprising a plurality of nucleic acid fragments and providing a set of target-specific hybridization probes that specifically bind to a plurality of target sequences present in the nucleic acid library. The method also includes the steps of contacting the off-target hybridization probes with the nucleic acid library under conditions whereby the off-target hybridization probes hybridize to the off-target sequences and contacting the target-specific hybridization probes with the nucleic acid library under conditions whereby the target-specific hybridization probes hybridize to the target sequences. The method also includes the steps of selecting a group of nucleic acid fragments from the nucleic acid library bound to the target-specific hybridization probes; and sequencing the group of nucleic acid fragments bound to the target-specific hybridization probes.

Presented herein is also a method of providing probes for off-target sequence capture in a targeted sequencing reaction. The method includes the steps of receiving a request for a set of target-specific hybridization probes. The method also includes the steps of contacting the target-specific hybridization probes with a reference nucleic acid library generated from a reference sample, the nucleic acid library comprising a plurality of nucleic acid fragments, to generate a reference group of target-specific and off-target nucleic acid fragments bound to the target-specific hybridization probes and separating the reference group of nucleic acid fragments bound to the target-specific hybridization probes from unbound nucleic acid fragments. The method also includes the steps of sequencing the reference group of nucleic acid fragments to generate reference sequencing data; identifying off-target sequences in the reference sequencing data; and providing a set of off-target hybridization probes based on the identified off-target sequences.

Presented herein is also a sequencing kit for reducing off-target capture in a targeted sequencing reaction that includes a set of off-target hybridization probes that specifically bind to a plurality of off-target sequences present in a nucleic acid library generated from a sample, the nucleic acid library comprising a plurality of nucleic acid fragments and a set of target-specific hybridization probes that specifically bind to a plurality of target sequences present in the nucleic acid library.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 2 shows genome browser views off-target reads from six samples of two cell lines with reads distribution at a targeted region (left side) and an off-target region (right side) with similar coverage;

FIG. 3 is a graph showing genomic distribution of off-target reads;

FIG. 11 is schematic representation of methods of reducing off-target capture in a targeted sequencing reaction used in conjunction with adaptor blockers according to embodiments of the disclosure;

FIG. 12 is schematic representation of methods of reducing off-target capture in a targeted sequencing reaction used in conjunction with attenuators according to embodiments of the disclosure;

FIG. 17 is a graph demonstrating coverage gain and drop on on-target regions, whereby dot represents read coverage of an on-target region in control (x-axis) and in the same sample with pre-cleaning (y-axis);

FIG. 18 is a graph demonstrating coverage gain and drop on on-target regions, whereby dot represents read coverage of an on-target region in control (x-axis) and in the same sample with pre-cleaning (y-axis);

FIG. 19 is a graph demonstrating coverage gain and drop on on-target regions, whereby dot represents read coverage of an on-target region in control (x-axis) and in the same sample with pre-cleaning (y-axis)

DETAILED DESCRIPTION

Figure 1:
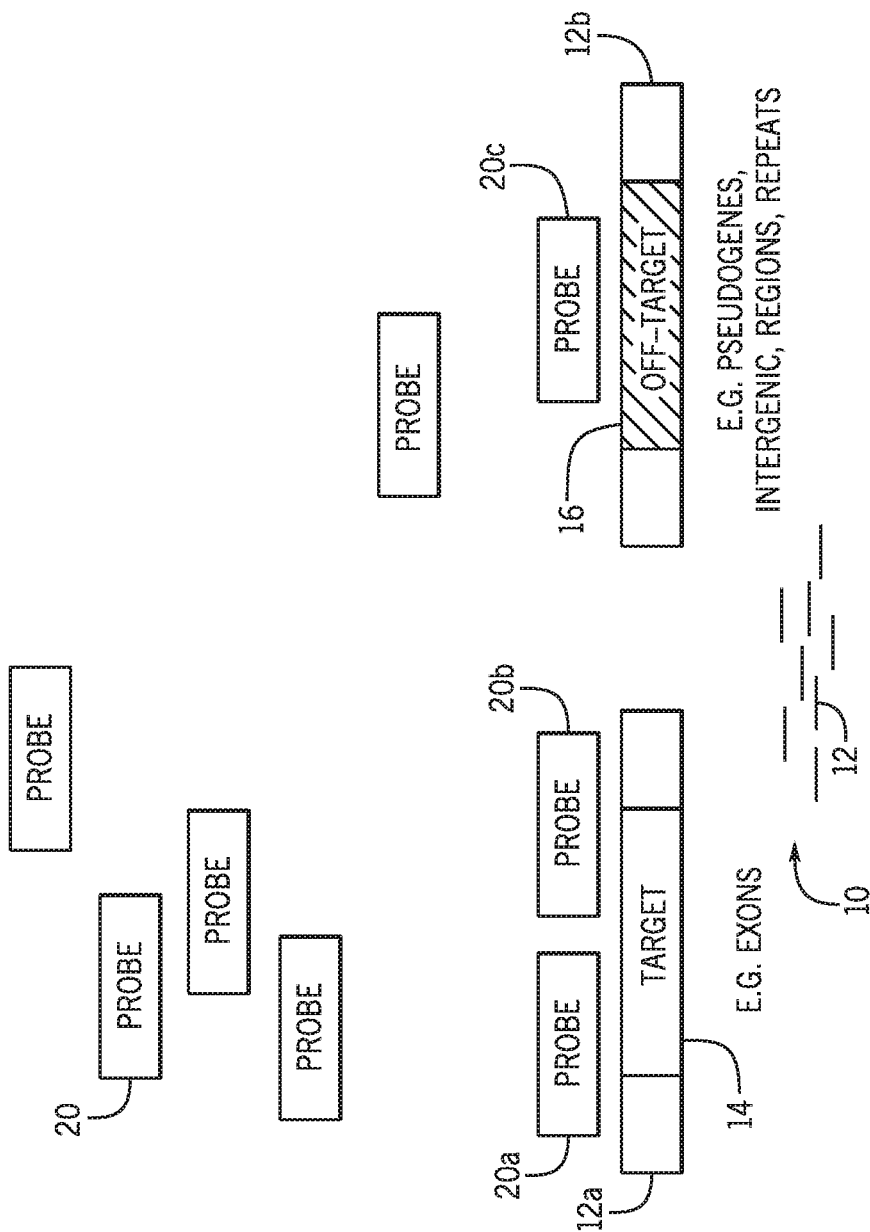
FIG. 1 is a schematic representation of target-specific hybridization probes binding to off-target fragments of a nucleic acid library.

Hybrid capture methods in which target sequences are selected via binding by hybridization probes are associated with a high off-target binding rate and low on-target specificity. The present techniques improve sequencing efficiency by reducing the presence of off-target sequences in a hybrid capture sequencing workflow using a data-guided approach. While certain techniques may use blockers or binding attenuators to influence probe binding, such approaches are not data-guided. For example, salmon sperm DNA may be used to prevent non-specific binding of probes to reaction surfaces. However, nonspecific blockers do not prevent the binding of target-specific probes to off-target sequences with similarity to target sequences. Target-specific probes have specificity for their intended targets. However, sequences present in off-target regions may be sufficiently similar to the target sequences (e.g., having short stretches of homology with the target, high string similarity) to permit at least some off-target binding of a target probe, albeit with lower specificity relative to the target sequence binding. Off-target binding is more prevalent in hybrid capture techniques relative to other targeted sequencing methodologies, in part because target-specific hybridization probes are typically longer oligonucleotides (80-120 mer) relative to the primers (25-30 mer) in PCR-based methods, which may facilitate probe binding to off-target sequences having sufficient similarity to the target sequences. PCR-based targeted sequencing typically requires both ends of the primer binding to a specific area. The double binding need makes random off-target binding slower to amplify compared to on-target binding, which in turn reduces off-target amplification. In another example, longer oligonucleotides are statistically more likely than shorter oligonucleotides to have contiguous base stretches within the oligonucleotides that are similar to the off-target sequences. Such complementary or high similarity contiguous stretches may contribute to off-target binding.

The present techniques use information about off-target sequences to improve hybrid capture and decrease the percentage of off-target capture. A hybrid capture sequencing reaction may acquire sequence data from off-target sequences as a result of undesired off-target binding of target-specific hybridization probes. While such off-target sequencing data is typically discarded, the present techniques harness the sequencing information of the off-target sequences for use in designing probes specific for these off-target regions. Using probes with high specificity for the off-target facilitates a reduction on the total number of off-target regions present in a pool of sequenced fragments. As a result of the data-guided approach, the percentage of off-target sequencing reads in a given sequencing run will be reduced. Accordingly, the present techniques provide the benefit of improving the efficiency of a sequencing device by reducing the total amount of raw data generated in a sequencing run. Further, the reduction in off-target reads present in the sequencing data also improves the efficiency of data analysis by reducing the amount of off-target sequence data to be identified and excluded from analysis.

Turning to the figures, embodiments of the present techniques include acquisition of off-target sequence data as an input for data-guided design of off-target hybridization probes. FIG. 1 is a schematic representation of off-target binding by target-specific hybridization probes that leads to the acquisition of off-target sequence data. Referring first to FIG. 1, a schematic representation of a hybrid capture workflow with off-target binding by a target-specific hybridization probe is illustrated. Such off-target binding as illustrated may be used to acquire sequencing data that is used to characterize the off-target sequences as provided herein. In a targeted sequencing hybrid capture workflow, target-specific hybridization probes are designed to hybridize to sequences present in regions of interest in a sample. The workflow includes preparation of a nucleic acid library 10 formed from a plurality of nucleic acid fragments 12 from the sample, such as a sample including genomic DNA (e.g., a human genome, an animal genome, a bacterial genome) or other nucleic acids. The nucleic library includes fragments having sequences from regions of interest (e.g., fragment 12a) that include target sequences 14 as well as fragments that are off-target (e.g., fragment 12b) having only off-target sequences 16. It should be understood that fragments 12 that include target sequences 14 may be formed entirely from regions of interest or may include other regions that are not of interest. The target-specific hybridization probes 20 are designed to be complementary to one or more target sequences 14 on a fragment 12. Accordingly, under hybridization conditions, one or more target-specific hybridization probes 20 (e.g., probes 20a, 20b) will bind to the complementary target sequences 14. This facilitates separation of fragments 12 that have the target sequences 14 from the fragments 12 that do not have the target sequences 14 (e.g., ones that have only off-target sequences 16) create a target-enriched sample for sequencing.

As provided herein, a target sequence 14 is a nucleic acid sequence present in a nucleic acid library that is complementary to a target-specific hybridization probe 20. Depending on the desired sequencing outcome, the target sequences 14 may be exonic sequences for exome sequencing. Accordingly, in some embodiments, the target-specific hybridization probes 20 are directed to target sequences 14 of exons. In another embodiment, the target sequences 14 may be custom sequences, or disease or allele-specific sequences. The target sequence 14 may be part of a region of interest in a nucleic acid sample, and the target-specific hybridization probe 20 may be designed based on various metrics to be specific for a portion of the region of interest.

As provided herein, a probe (e.g., a target-specific hybridization probe 20) is an oligonucleotide, such as a single-stranded nucleic acid molecule. The target-specific hybridization probe 20 may be part of a set or panel of target-specific hybridization probes 20. The target-specific hybridization probes 20 may be 80-120 bases in length, 80-100 bases in length, 90-110 bases in length, 100-120 bases in length, etc. In certain embodiments, if the target-specific hybridization probe 20 is 80-120 bases in length, at least 30-50 of the bases of the target-specific hybridization probe 20 are complementary to the target sequence 14. It should be understood that a hybrid capture sequencing reaction may be performed using a set of target-specific hybridization probes 20, wherein different probes are representative of different target sequences 14 in the nucleic acid library. For example, the set of target-specific hybridization probes 20 may be representative of at least 2000 different target sequences 14, at least 5000 different target sequences 14, at least 10,000 different target sequences 14, and so on. Further, while the disclosed embodiments are discussed with regard to hybrid capture technologies, incorporation of the techniques provided herein may also be implemented with PCR or amplicon-based sequencing techniques. In such embodiments, the target-specific hybridization probes 20 may be on the order of 20-40 bases in length.

In certain embodiments, the target-specific hybridization probes 20 may have modifications that facilitate separation of bound fragments 12 from the unbound fragments 12. Such modifications may include biotinylation of the probe to facilitate selection via streptavidin (e.g., streptavidin beads). However, it should be understood that the probes as provided herein may be coupled to other an affinity binding molecule that is part of a binding pair. For example, biotin and streptavidin, biotin and avidin, or digoxigenin and a specific antibody that binds digoxigenin are examples of specific binding pairs. The affinity binding molecule may be an antibody ligand capable of being conjugated to a nucleotide. In certain embodiments, the modification is provided at the 5' or the 3' end of the probe. Further, in other embodiments, the probes may be unmodified. The target-specific hybridization probes 20 may also include unique barcodes or sequences that facilitate identification. Such sequences may part of a region of the probe 20 that is non-complementary to the target sequence 14. The target-specific hybridization probes 20 may be in solution or immobilized on a solid support (e.g., an array).

As shown in FIG. 1, fragment 12b includes an off-target sequence 16 to which a target-specific hybridization probe 20c is bound in an example of off-target binding. Once bound to the target-specific hybridization probe 20c, the off-target fragment 12b is separated from the rest of the nucleic acid library 10 along with the fragments 12 that include target sequences 14 and processed through the sequencing reaction. Accordingly, the off-target sequence read from the fragment 12b will be included in the sequencing data. While the probe 20c has higher specificity for its target sequence 14 relative to the off-target sequence 16, the binding conditions nonetheless permit binding of the some of the target-specific hybridization probe 20c to the off-target sequence 16. In other words, certain off-target sequences 16 may share sufficient similarity to the target sequence 14 for the probe 20c to permit the binding to occur.

As provided herein, an off-target sequence 16 is a sequence that is not an intended target of one or more of the target-specific hybridization probes 20. In one example, if the target-specific hybridization probes 20 are for exome sequencing, an off-target sequence 16 may be an intronic or intergenic sequence. In certain embodiments, a target-specific hybridization probe 20 is capable of binding to an off-target sequence 16 with lower specificity than for the intended target sequence.

An examination of off-target sequences was performed to demonstrate that the off-target sequences are relatively stable between samples. FIG. 2 shows sequencing results for systematic off-target regions that were highly reproducible across different samples and replicates from 6 samples of two cell lines as shown in genome browser views of the reads distribution at (a) a targeted region and (b) an off-target region with similar coverage. Each track is one sample. FIG. 2 demonstrates that off-target binding tends to be stable and that the incidence, distribution and representation of the off-targets were systematic rather than random.

FIG. 3 is a graph showing genomic distribution of off-target reads. Off-target regions showed similar coverage across different replicates. In the samples studied, 45% of the off-target sequences were located in introns, 48% in intergenic regions, and 7% in exons.

Figure 5:
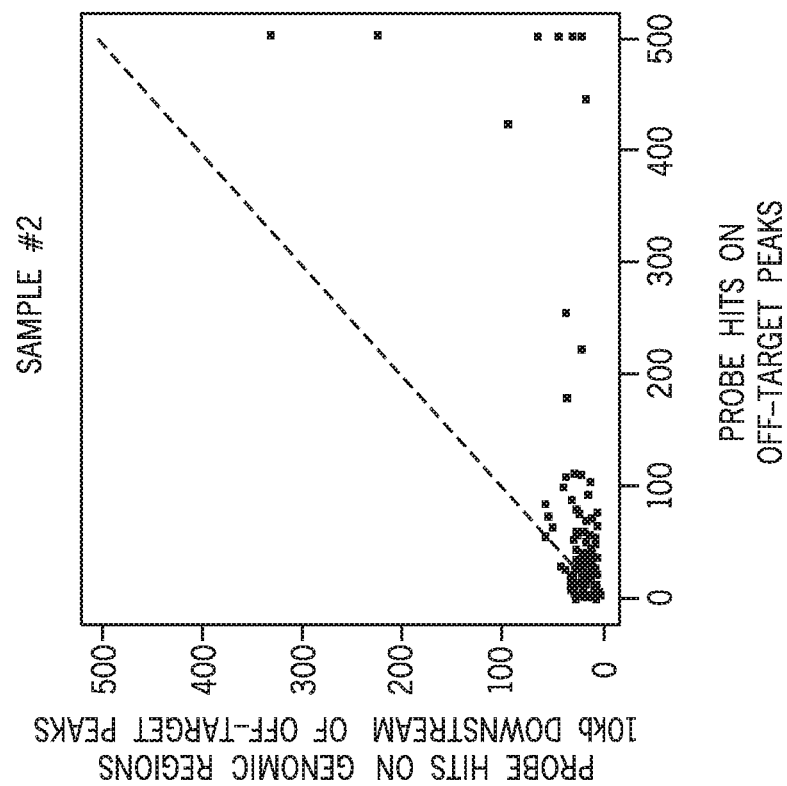
FIG. 5 is a graph demonstrating similarity between target probes and off-target peaks for a second sample.
Figure 4:
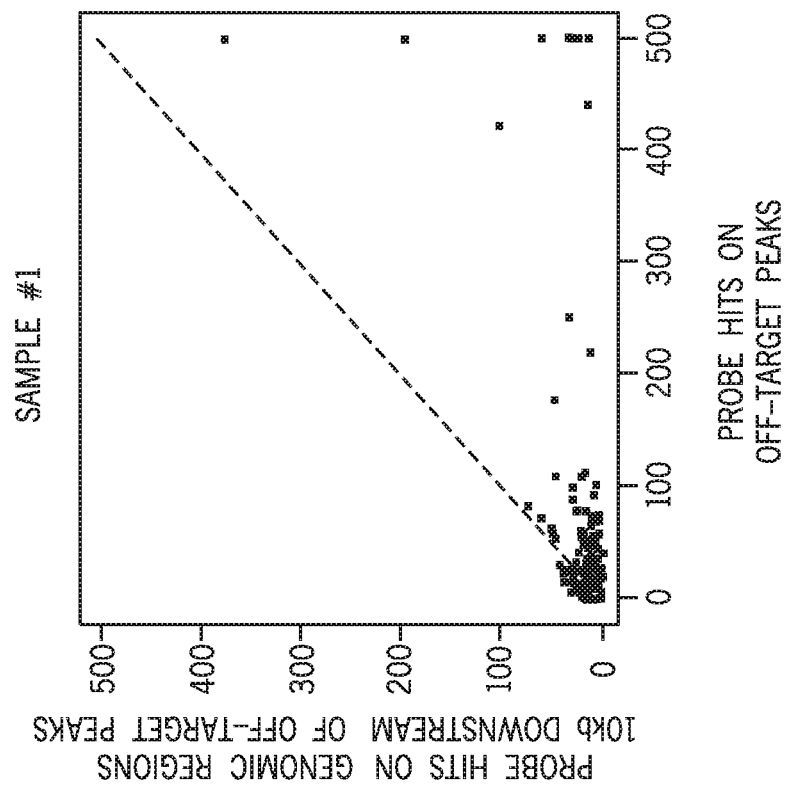
FIG. 4 is a graph demonstrating similarity between target probes and off-target peaks for a first sample.

The sequence similarities between the off-target regions and capture probes also indicate that off-target reads were likely pulled down by probes, rather than by random binding. FIGS. 4-5 show graphs demonstrating similarity between target probes and off-target peaks. Systematic off-target regions had sequence similarity with target probes shown in different samples. The 10 kb downstream regions were subject to the same analysis as negative control. Each dot represents the number of probes sharing sequence similarity with an off-target peak (x-axis) and with its 10 kb downstream region (y-axis). Accordingly, the data show that the off-target sequences are likely to be specific and reproducible between samples for a given set of target-specific hybridization probes. From the sequencing data it was observed that there are off-target regions with coverage significantly higher than general background and comparable to or even higher than actual targets. If ranked by contribution to coverage, a portion of off-target loci contribute to the majority of off-target reads. If fragments of these regions can be reduced during sequencing, coverage on actual target can be improved consequently. To that end, the present techniques include off-target hybridization probes that are specific for the off-target sequences that are stable and/or prevalent between samples. Further, in certain embodiments, off-target hybridization probes may be designed for the off-target loci that contribute to the majority of off-target reads.

Figure 6:
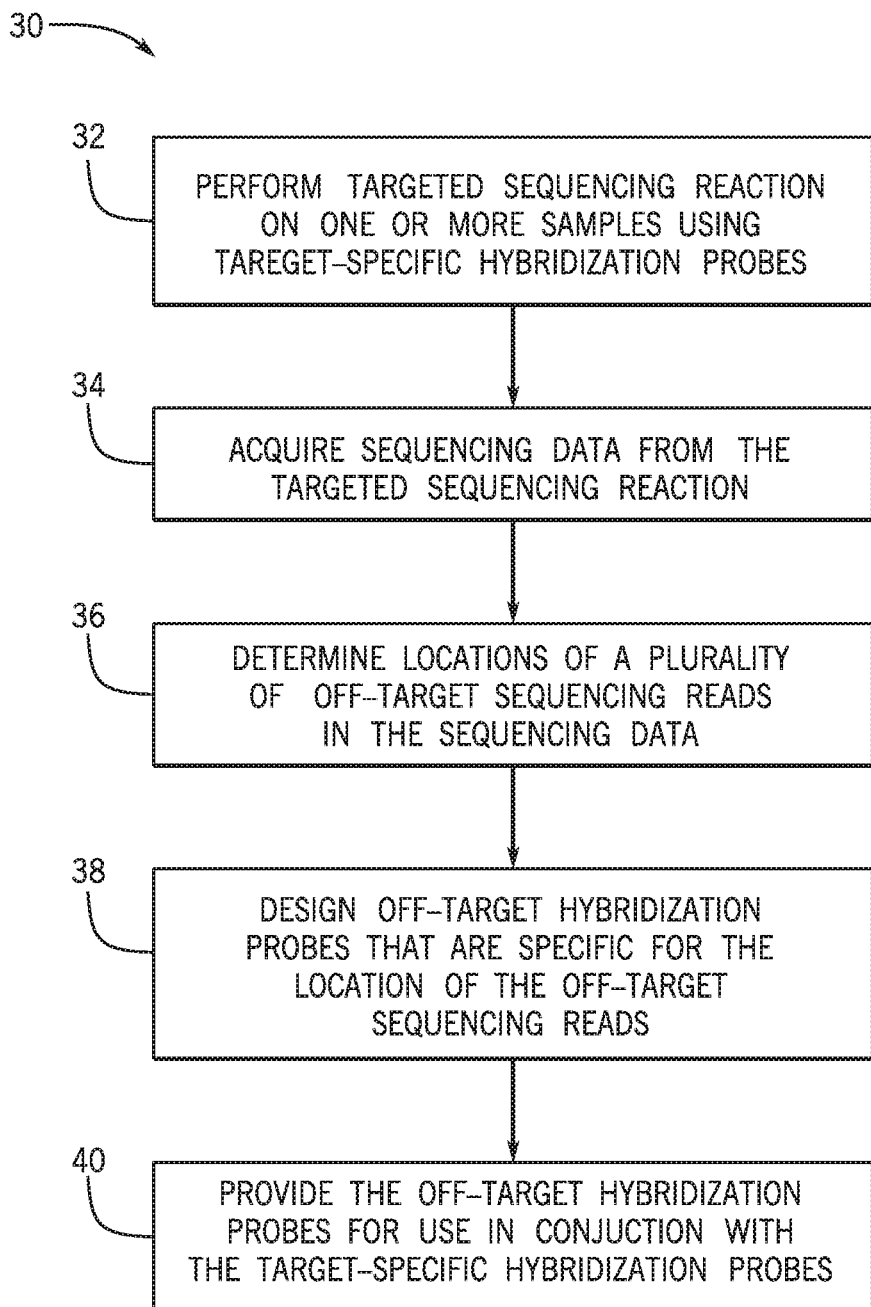
FIG. 6 is a flow diagram of a method of providing off-target hybridization probes according to embodiments of the disclosure.

FIG. 6 is a flow diagram of a method 30 for identifying off-target sequences as provided herein. Targeted sequencing (e.g., hybrid capture sequencing) using a set of target-specific hybridization probes is performed (step 32) and sequencing data acquired (step 34 to identify loci of high-frequency off-target reads in the hybrid capture sequencing data (step 36). Based on the loci of the off-target reads, off-target hybridization probes are designed (step 38) and provided for use in conjunction with the target-specific hybridization probes (step 40).

As provided herein, sequencing data may include raw data as well as base call data for the sequenced fragments of the nucleic acid library. Further, the sequencing data may have undergone alignment and assembly so that the genome loci of the assembled fragments can be identified. Accordingly, the sequence data may include sequence information and location information for the assembled fragments such that off-target data is identifiable based at least in part on the location of the sequenced fragments. In addition, the sequencing data may include coverage data of off-target sequence reads so that the off-target prevalence as well as locations may be assessed. In this manner, the highest prevalence sequence reads (i.e., highest coverage) for various off-target loci may be identified. In certain embodiments, the off-target reads are ranked according to coverage to identify the highest frequency off-target loci. The off-target hybridization probes may be designed based on the highest 50, 100, 1000, or 2000 loci. In one embodiment, the design is based on a user-specified number of the ranked sequences.

In one embodiment, the method 30 may be performed as part of a workflow for generating a panel of target-specific hybridization probes. Based on a request for a particular panel of target-specific hybridization probes, the method 30 is initiated on a reference sample to identify and assess the off-target sequences. The reference sample may be an internal standard that is known to be a high quality sample. In another embodiment, the method 30 is initiated upon receipt of a customer request for a custom panel of target-specific hybridization probes. As part of synthesizing the custom panel, the method 30 is performed to identify potential off-target sequences. Accordingly, the method 30 may be performed in response to a user or customer input.

Based on the identified off-target sequences, a set of off-target hybridization probes may be identified and synthesized to be provided as part of a sequencing kit. The off-target hybridization probes may be an optional add-on item to improve sequencing yield and reduce off-target sequence capture. In another embodiment, the method 30 may also include generating an estimate of sequencing cost reduction for the reference sample based on an estimated reduction in off-target sequencing reads. For example, if a typical hybrid capture sequencing run generates 60% target reads and 40% off-target reads, then 40% of the cost of sequencing is attributable to off-target sequences. If the set of off-target hybridization probes is designed to correspond to off-target sequences that represent about 50% of the off-target coverage in the reference sequencing data, then the off-target hybridization probes are capable of reducing off-target reads by 50%. Accordingly, a sequencing run using the off-target hybridization probes to reduce off-target capture may be estimated to lower costs by 20% relative to the control. In this manner, a user may determine if the cost of the off-target hybridization probes will generate sufficient savings on sequencing. The method 30 may also permit dynamic estimates based on variable user inputs. For example, reducing the total number of off-target sequences of the off-target hybridization probes will reduce probe cost, but may be associated with a slight increase in off-target sequence capture, resulting in an associated rise in estimated sequencing costs relative to a selection of a higher number of off-target sequences of the off-target hybridization probes. In another embodiment, the user may provide a total sequencing budget, including any target and off-target probe costs, for a given sample, and a determination may be made if cost savings can be achieved using the off-target hybridization probes.

As provided herein, an off-target hybridization probe (e.g., off-target hybridization probe 60, see FIGS. 8-13) has higher specificity for an off-target sequence (e.g., off-target sequence 16, see FIG. 1) relative to any target sequences. An off-target hybridization probe is an oligonucleotide, such as a single-stranded nucleic acid molecule. The off-target hybridization probe may be part of a set of off-target hybridization probes. The off-target hybridization probes may be 80-120 bases in length, 80-100 bases in length, 90-110 bases in length, 100-120 bases in length, etc. In certain embodiments, if the off-target hybridization probe is 80-120 bases in length, at least 30-50 of the bases of the off-target hybridization probe are complementary to the off-target sequence. Further, while the disclosed embodiments are discussed with regard to hybrid capture technologies, incorporation of the techniques provided herein may also be implemented with PCR or amplicon-based sequencing techniques. In such embodiments, the off-target hybridization probes 20 may be on the order of 20-40 bases in length. In one embodiment, the off-target hybridization probes may be about the same length as the target specific hybridization probes. In another embodiment, the off-target hybridization probes may be a different length (e.g., shorter or longer) relative to the target specific hybridization probes.

It should be understood that a targeted sequencing reaction may be performed using a set of target-specific hybridization probes 20 together with (e.g., in parallel or in sequence) off-target hybridization probes, wherein off-target hybridization probes are representative of different off-target sequences in the nucleic acid library. For example, the set of off-target hybridization probes may be representative of at least 50 different off-target sequences, at least 100 different off-target sequences, at least 10000 different off-target sequences, and so on. In another embodiment, a set of target sequences represents a greater number of different sequences than a set of off-target sequences for the probes used in a hybrid capture sequencing as provided herein. For example, a ratio of the number of different target sequences in the target-specific hybridization probes to the number of different off-target sequences in the off-target hybridization probes may be 2:1, 3:1, 4:1, 5:1 or greater in certain embodiments. There are certain advantages to providing a limited number of off-target hybridization probes due to the cost of manufacturing additional probes for use. Accordingly, the ranking of the prevalence of off-target sequences may be used to permit user selection of a number of desired off-target hybridization probes. Further, certain highly prevalent off-target sequences may be present in the total pool of off-target sequences to such a high degree that having a limited number of off-target hybridization probes specific for highly prevalent off-targets may nonetheless yield a high reduction in off-target sequence capture.

In certain embodiments, the off-target hybridization probes may have modifications that facilitate separation of bound fragments from the unbound fragments. Such modifications may include biotinylation of the probe to facilitate selection via streptavidin (e.g., streptavidin beads). However, it should be understood that the probes as provided herein may be coupled to other an affinity binding molecule that is part of a binding pair. For example, biotin and streptavidin, biotin and avidin, or digoxigenin and a specific antibody that binds digoxigenin are examples of specific binding pairs. In certain embodiments, the modification is provided at the 5' or the 3' end of the probe. Further, in other embodiments, the probes may be unmodified.

The off-target hybridization probes may also include unique barcodes or sequences that facilitate identification. Such sequences may part of a region of the probe that is non-complementary to the off-target sequences. The off-target hybridization probes may be in solution or immobilized on a solid support (e.g., an array). In another embodiment, the target-specific hybridization probes and the off-target hybridization probes are provided as similar length probes, i.e., all within a certain range. Accordingly, in a specific embodiment, the target-specific hybridization probes and the off-target hybridization probes are all in a range of 80-120 bases in length. In another embodiment, the target-specific hybridization probes and the off-target hybridization probes are all in a range of 20-40 bases in length. In yet another embodiment, the target-specific hybridization probes have a length all in a first range and the off-target hybridization probes have a length all in a second range, whereby the first range and the second range are different. In one embodiment, the first range encompasses longer probe lengths than the second range. In another embodiment, the first range encompasses shorter probe lengths than the second range.

In certain embodiments of the disclosure, providing the off-target hybridization probes comprises providing the off-target hybridization probes as part of a sequencing kit for use with the target-specific hybridization probes. The off-target hybridization probes may be specific for only certain types of off-target sequences (e.g., introns, intergenic regions). In this manner, a user may select the off-target sequences of interest. In another embodiment, providing the off-target hybridization probes comprises providing the off-target hybridization probes as part of a request or order for a custom target-specific hybridization probe panel. When the request for the custom panel is received, the synthesis facility may also perform the steps of the method 30 to determine the off-target sequences of concern (e.g., highly prevalent off-target sequences) for the custom panel and provide off-target hybridization probes to reduce off-target reads from these identified off-target sequences.

In another embodiment, a universal set of off-target hybridization probes may be provided. That is, regardless of the particular panel of target-specific hybridization probes used, certain off-target reads may be common across a species. In one implementation, a species-specific set of off-target hybridization probes may be used to de-host a sample, such as in microbiology, infectious disease, food safety, and quality monitoring. A universal set and/or a species-specific set may be determined using the data-guided techniques as provided herein. For example, the universal set or the species-specific set may be selected by performing sequencing on reference samples using different panels of target-specific hybridization probes (e.g., using a plurality of human-specific panels or using a plurality of cancer-specific panels) and selecting the top-ranked (i.e., most prevalent) off-target sequences from the sequencing data from all of the different panels to design the off-target hybridization probes. In one embodiment, the top-ranked set may include only the off-target sequences that are common between samples sequenced using different panels. In another embodiment, the top-ranked set may be representative of a pool of all of the off-target sequences in the sequencing data using the different panels, such that some sequences in the pool are only off-target for a given panel. However, the top-ranked set will nonetheless include a number of off-target reads represented in the sequencing data for each sample such that the universal set, when used, will reduce off-target capture when used in conjunction with any of the panels.

Figure 7:
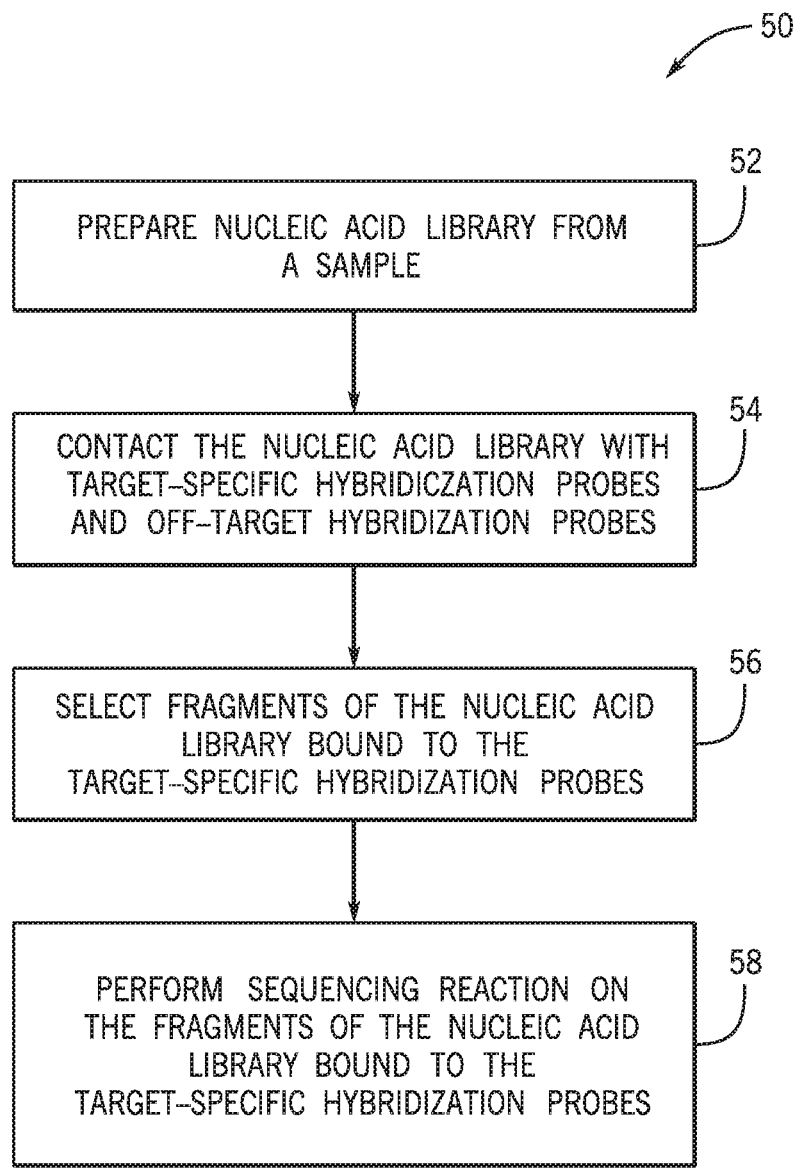
FIG. 7 is a flow diagram of a method of reducing off-target capture in a targeted sequencing reaction according to embodiments of the disclosure.

Also provided herein are methods of implementing targeted sequencing using the off-target hybridization probes as provided herein. FIG. 7 is a method 50 of reducing off-target capture in a targeted sequencing reaction. The nucleic acid library may be prepared (step 52) according to a desired technique to facilitate fragment formation of the appropriate size. The library, once prepared, is contacted with off-target hybridization probes and target-specific hybridization probes (step 54), either in sequence or in parallel, under conditions that permit probe binding. For example, double-stranded fragments may be denatured to yield single-stranded fragments. The fragments bound to the target-specific hybridization probes are selected for sequencing (step 56), e.g., via the techniques disclosed in FIGS. 8-10. In one embodiment, the selecting is accomplished by separating fragments bound to the target-specific hybridization probes from fragments bound to off-target hybridization probes as well as from fragments not bound to any probes. In another embodiment, the selecting is accomplished by first removing fragments bound to off-target hybridization probes and then removing fragments not bound to any probes. Once selected, the fragments bound to the target-specific hybridization probes are sequenced (step 58) to yield sequencing data with a reduction in off target sequence reads relative to a control. For example, a control of the sample that is contacted with only target-specific hybridization probes and not with off-target hybridization probes.

Figure 8:
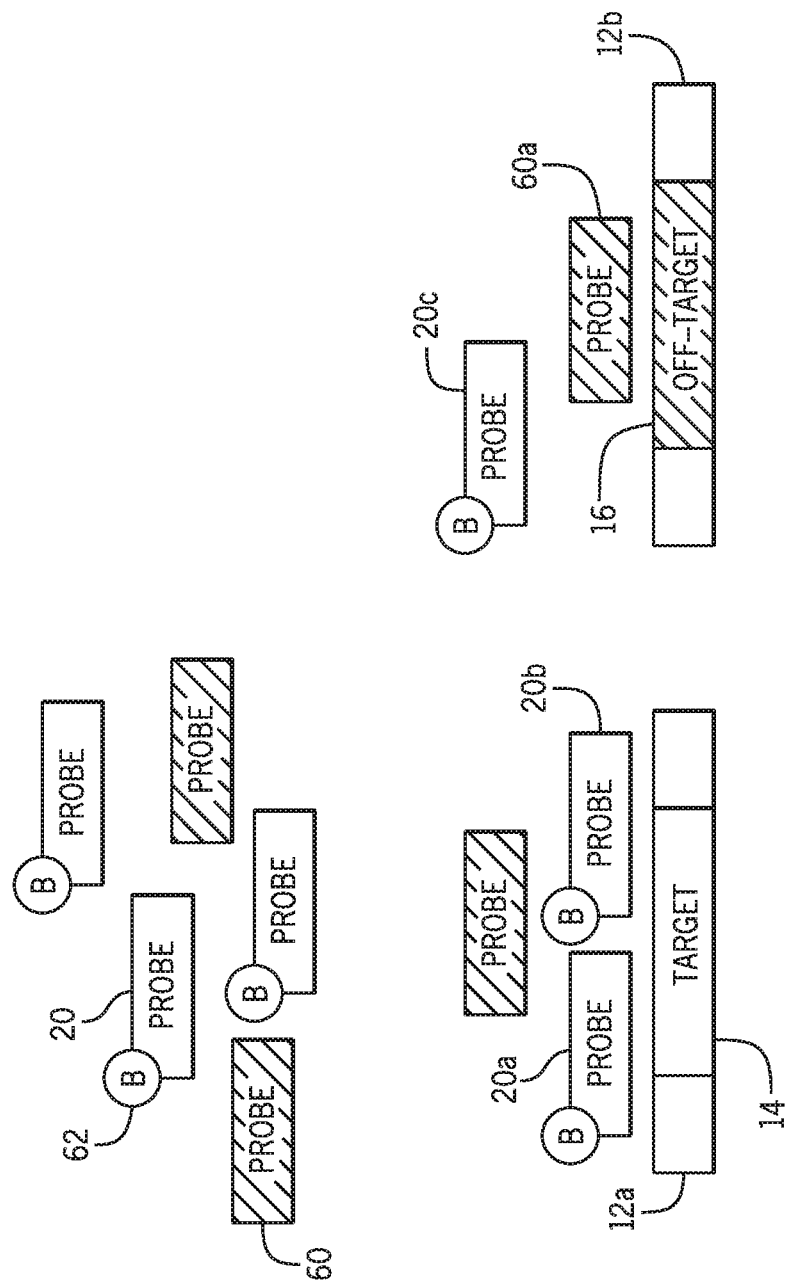
FIG. 8 is schematic representation of a competitive blocking method of reducing off-target capture in a targeted sequencing reaction according to embodiments of the disclosure.

FIG. 8 is a schematic illustration of an implementation of the method 50 using competitive blocking. In the illustrated embodiment, off-target hybridization probes 60 are synthesized as 5' un-modified (without biotin) and used in a hybridization reaction along with (i.e., at the same time as or in the same solution) target-specific hybridization probes 20 with a biotinylated end 62. The unmodified off-target hybridization probes 60 compete for binding to the off-target loci with the target-specific hybridization probes 20. This in turn makes the off-target loci inaccessible or less accessible to the target-specific hybridization probes 20. Separation of the target-specific hybridization probes 20 bound to the fragments 12 may be accomplished using streptavidin, which binds to the biotinylated ends 62 and not to the off-target hybridization probes 60. The resulting group of separated target-specific hybridization probes 20 bound to the fragments 12 is enriched for target sequences 14 and has a reduction in off-target sequences 16 relative to a control group in which no off-target hybridization probes 60 are used.

Figure 9:
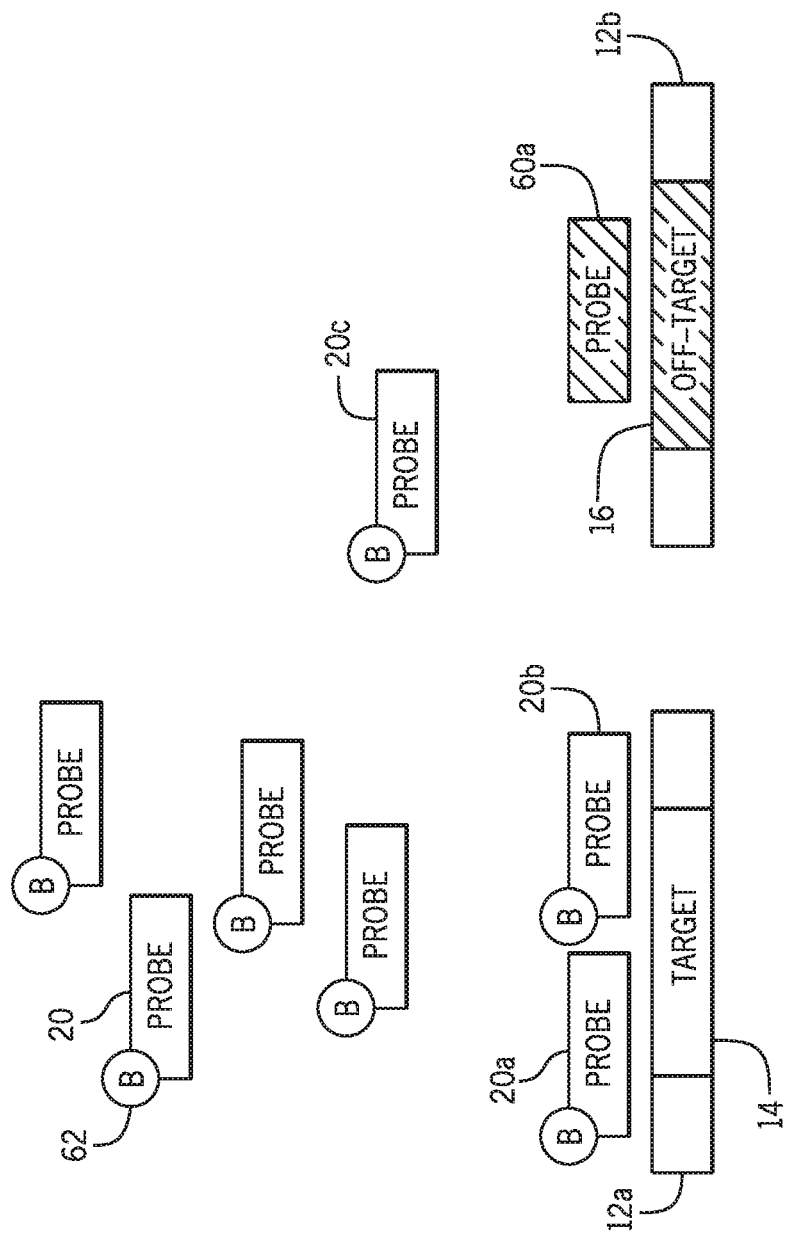
FIG. 9 is schematic representation of a pre-blocking method of reducing off-target capture in a targeted sequencing reaction according to embodiments of the disclosure.

FIG. 9 is a schematic illustration of an implementation of the method 50 using pre-blocking. In the illustrated embodiment, unmodified off-target hybridization probes 60 are first contacted with the library to pre-block the corresponding off-target sequences 16. The target-specific hybridization probes 20 are contacted with the library after the pre-blocking has occurred, i.e., only after the off-target hybridization probes 60 are bound. The off-target hybridization probes 60 are synthesized as 5' un-modified (without biotin) while the target-specific hybridization probes 20 have biotinylated ends 62. Separation of the target-specific hybridization probes 20 bound to the fragments 12 may be accomplished using streptavidin, which binds to the biotinylated ends 62 and not to the off-target hybridization probes 60. The resulting group of separated target-specific hybridization probes 20 bound to the fragments 12 is enriched for target sequences 14 and has a reduction in off-target 16 sequences relative to a control group in which no off-target hybridization probes 60 are used.

Figure 10:
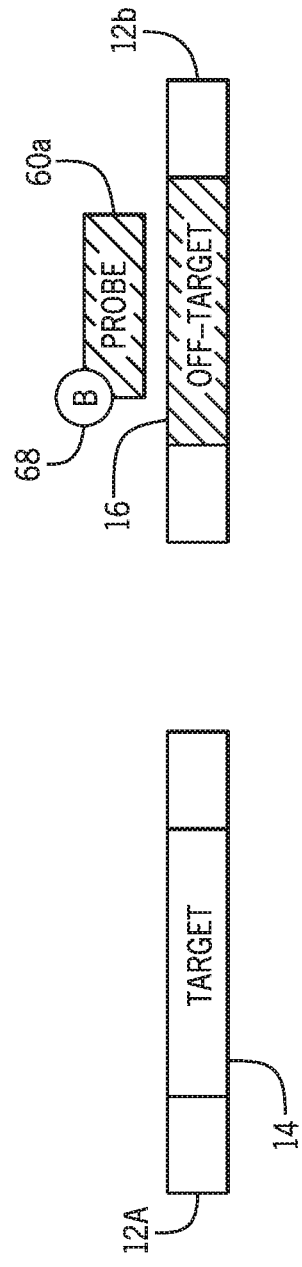
FIG. 10 is schematic representation of a pre-clearing method of reducing off-target capture in a targeted sequencing reaction according to embodiments of the disclosure.

FIG. 10 is a schematic illustration of an implementation of the method 50 using pre-clearing. In the illustrated embodiment, modified off-target hybridization probes 60, shown with biotinylated ends 68, are first contacted with the library and permitted to bind with corresponding off-target sequences 16. The off-target hybridization probes 60 bound to the fragments that include off-target sequences 16 are pulled out using with streptavidin beads to pre-clear, i.e., pull the undesirable off-target loci out of the reaction. The pre-cleared supernatant is retained for the subsequent hybrid capture reaction with the modified target-specific hybridization probes 20 having biotinylated ends 62. The target sequences 14 remaining that are bound to the target-specific hybridization probes 20 are separated from any unbound fragments and then sequenced. The resulting group of pre-cleared and separated target-specific hybridization probes 20 bound to the fragments 12 is enriched for target sequences 14 and has a reduction in off-target 16 sequences relative to a control group in which no off-target hybridization probes 60 are used.

It should be understood that the target-specific hybridization probes 20 and the off-target hybridization probes 60 as provided herein may be used in conjunction with blockers or other approaches used in hybrid capture to reduce probe self-annealing, sticky probes, or nonspecific binding. FIGS. 11-12 illustrate examples of approaches that may be combined, either in parallel or in sequence, with the off-target hybridization probes 60 and the embodiments disclosed herein for improved results. These examples are merely illustrative, and are not intended to be limiting. FIG. 11 shows an example of antisense adapter blockers 70 that prevent adapters 72 from self-annealing. FIG. 12 shows an example of one or more probe attenuators 76 that are antisense for target-specific hybridization probes 20 to a "hyper" or sticky target sequence 14.

In one embodiment, the off-target hybridization probes are specific for the highly enriched off-target regions to provide reduction of the most-prevalent off-target reads. Where an off-target sequence has a highly similar sequence to the actual target region, use of an off-target hybridization probe specific for that highly similar sequence could cause an unintended coverage drop for the target region having the similar sequence. To prevent this from happening, in one embodiment, off-target hybridization probes may be selected only from off-target regions having less than a threshold similarity with a target sequence according to one or more similarity metrics (e.g., Damerau-Levenshtein distance, Needleman-Wunsch algorithm, BLAST score). In one embodiment, a threshold percent identity or identity score is used to qualify off-target hybridization probes, with only off-target sequences having less than a predetermined percent identity (e.g., less than 50%, less than 25%) with a target sequence being qualified. For example, in one embodiment, only off-target sequences that do not contain matches of 15 or more contiguous bases with a target sequence will be qualified for off-target hybridization probe design. Those off-target sequences with 15 or more contiguous bases in common with a target sequence are not used as the basis for any off-target hybridization probes, even if such off-target sequences are highly prevalent. In another example, because the loci of off-target sequences are known, the sequence for which the off-target hybridization probe is specific can be shifted 5' or 3' away from the highly similar region, e.g., moved 20-50 bases 5' or 3' such that the targeted region has a lower similarity score.

Figure 13:
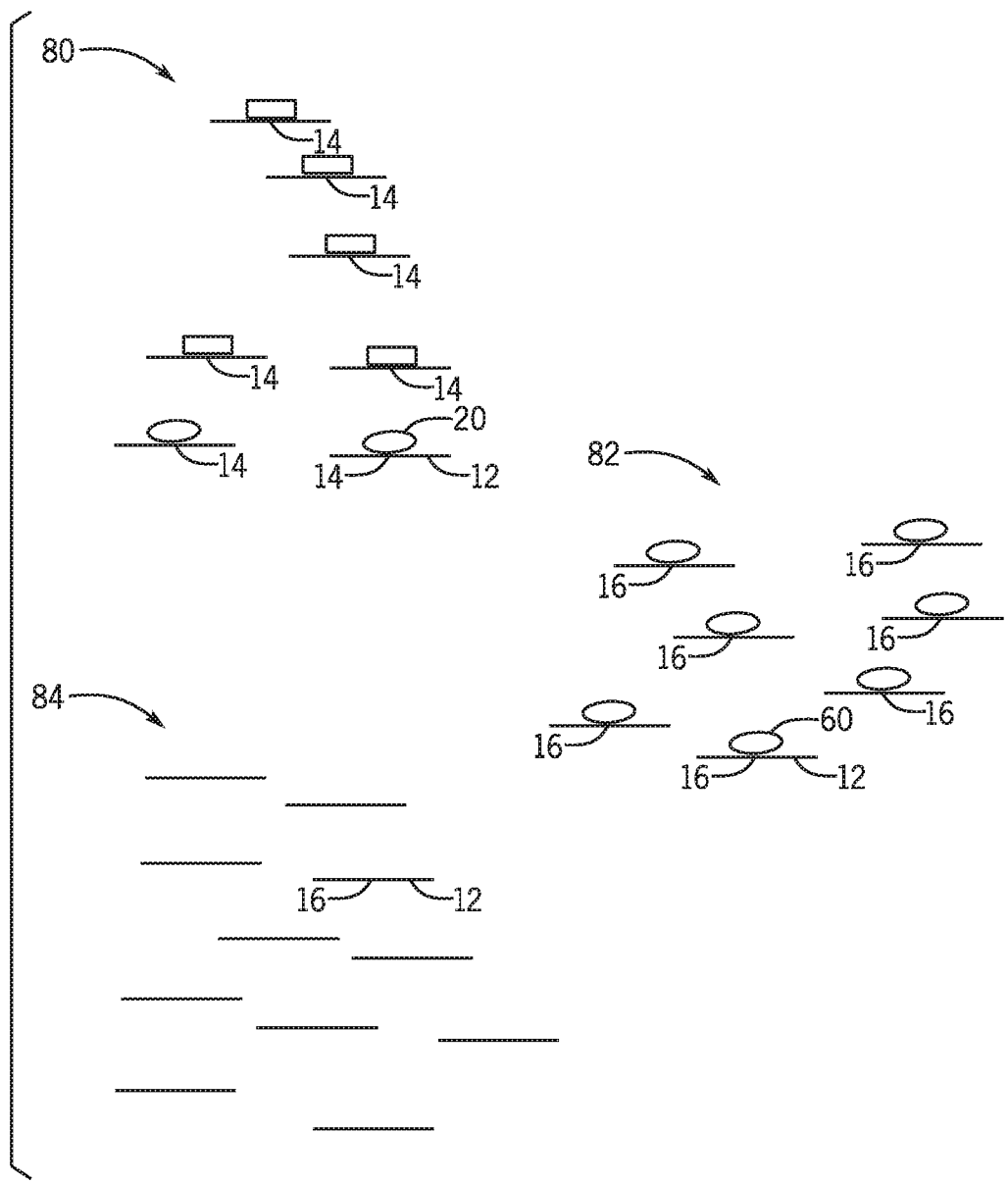
FIG. 13 is schematic representation of fragments of a nucleic acid library separated according to probe binding according to embodiments of the disclosure.

As shown in FIG. 13, the nucleic acid library used in a hybrid capture sequencing as provided herein is contacted with target-specific hybridization probes 20 and off-target hybridization probes 60, either in sequence or in parallel. The contacting yields a target group 80 of fragments 12 including target sequences 14 bound to the target-specific hybridization probes 20, an off-target group 82 of fragments 12 including off-target sequences bound to the off-target hybridization probes 60, and an unbound group 84 of fragments 12 that are not bound to any probes. The unbound group 84 includes sequences for which no target-specific hybridization probes 20 or off-target hybridization probes 60 were designed. Selection of the target group 80 for sequencing and not the off-target group 82 and/or the unbound group 84 may be accomplished via the techniques disclosed herein. For example, target-specific hybridization probes 20 that include a biotin modification may be selected by binding with avidin or streptavidin coupled to beads or a support. Where the off-target hybridization probes 60 are unmodified, the off-target group and the unbound group 84 can be removed by washing.

In another embodiment, it may be desirable to retain the off-target group 82 to assess probe quality. The pre-clearing technique (see FIG. 10) may be used to pull out the fragments 12 bound to the off-target hybridization probes 60, i.e., the off-target group 82. These fragments 12 in the off-target group 82 may be sequenced and evaluated for the presence of any target sequences 14. Any target sequences present in the off-target group 82 may then be assessed for similarity to one or more off-target hybridization probes, which in turn may be removed from the set or redesigned.

In one example, to find the consistent off-target regions, a set of representative samples, e.g. a set of samples of different cell lines/tissues sequenced with good quality, were selected. Firstly, on-target reads were filtered out of the sequencing data, then regions highly enriched for off-target reads were called using peak-calling tools GEM for the ENCODE project. However, other peaking calling algorithms may also be used. Overlapping peaks from different samples were then extracted and peaks within 50 bp were merged and only those that are 400 bp or more away from the targets were kept. The off-target peaks that were identified previously were sorted by the average coverage. According to the ranking those with significantly high coverage were choose to design reducers against. Off-target hybridization probes were designed to be specific for off-target regions that contributed to about 50% of the total off-target reads. DesignStudio (Illumina Inc.) was be utilized to design the off-target hybridization probes, representative of approximately 2000 off-target sequences.

Figures 14, 15, 16:
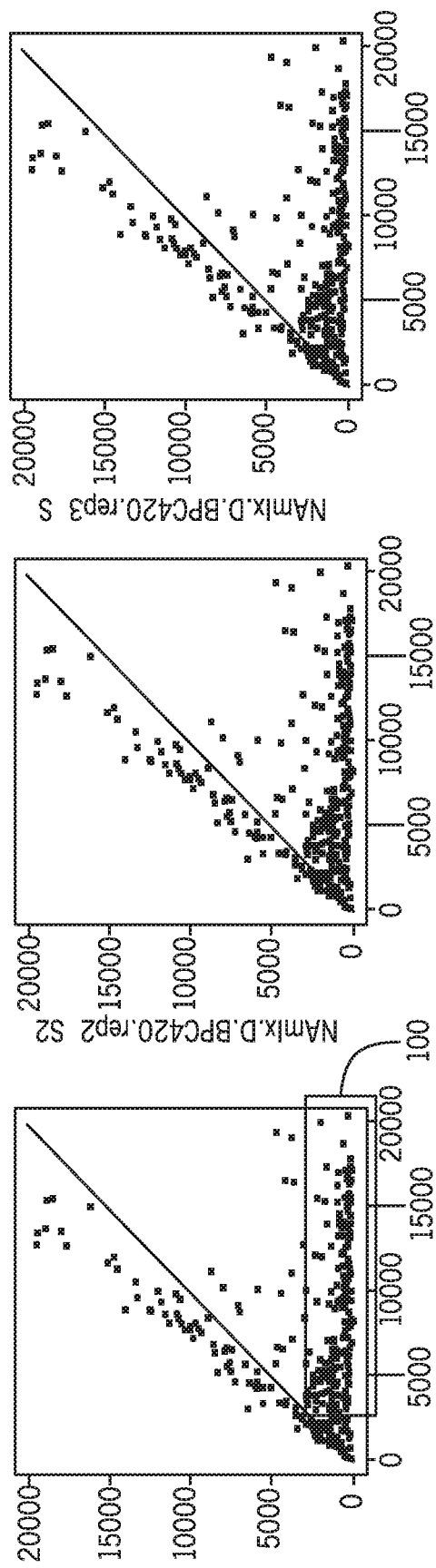
FIG. 14 is a graph demonstrating significant coverage drop on off-target peaks after pre-clearing, with each dot represents read coverage of an off-target peak in control (x-axis) and in the same sample from the pre-clearing protocol (y-axis)
FIG. 15 is a graph demonstrating significant coverage drop on off-target peaks after pre-clearing, with each dot represents read coverage of an off-target peak in control (x-axis) and in the same sample from the pre-clearing protocol (y-axis)
FIG. 16 is a graph demonstrating significant coverage drop on off-target peaks after pre-clearing, whereby each dot represents read coverage of an off-target peak in control (x-axis) and in the same sample from the pre-clearing protocol (y-axis)

Using off-target probe design as outlined herein, FIGS. 14-16 show graphs demonstrating significant coverage drop on off-target peaks after pre-clearing. Each dot represents read coverage of an off-target peak in control (x-axis) and in the same sample from the pre-clearing protocol (y-axis). The box 100 in FIG. 14 highlights the significant difference in the read coverage of the control vs. the pre-clearing protocol.

FIGS. 17-19 show graphs demonstrating coverage gain and drop on on-target regions. Each dot represents read coverage of an on-target region in control (x-axis) and in the same sample with pre-cleaning (y-axis). The area 104 highlights the coverage gain whereas the box 102 underlines coverage drop as shown in FIG. 17.

The techniques provided herein address the problem of a high off-target capture rate by using guided information from data analysis on the off-target regions. Prior attempts to solve this issue have utilized Cot1, tRNA, poly(dI-dC), adapter blockers and blockers for high-representation genes (e.g. anti-mitochondrial gene blockers). In contrast to those methodologies, the methods presented herein represent the first data driven approach. Furthermore, using off-target hybridization probes to clean or remove the unwanted DNA fragments out of sample libraries prior to target-specific binding is a novel approach. Further, the identified systematic off-target regions that are stable between samples as well as different sets or panels of hybridization probes may not necessarily be identified by the conventional wisdom. For example, they may not necessarily be identifiable repetitive elements such as Alu, SINE, LINE, or etc. In some embodiments, the approach described herein can be applied to other genomes to develop specie-specific off-target hybridization probes for metagenomic applications or contamination elimination in sample prep.

Figure 20:
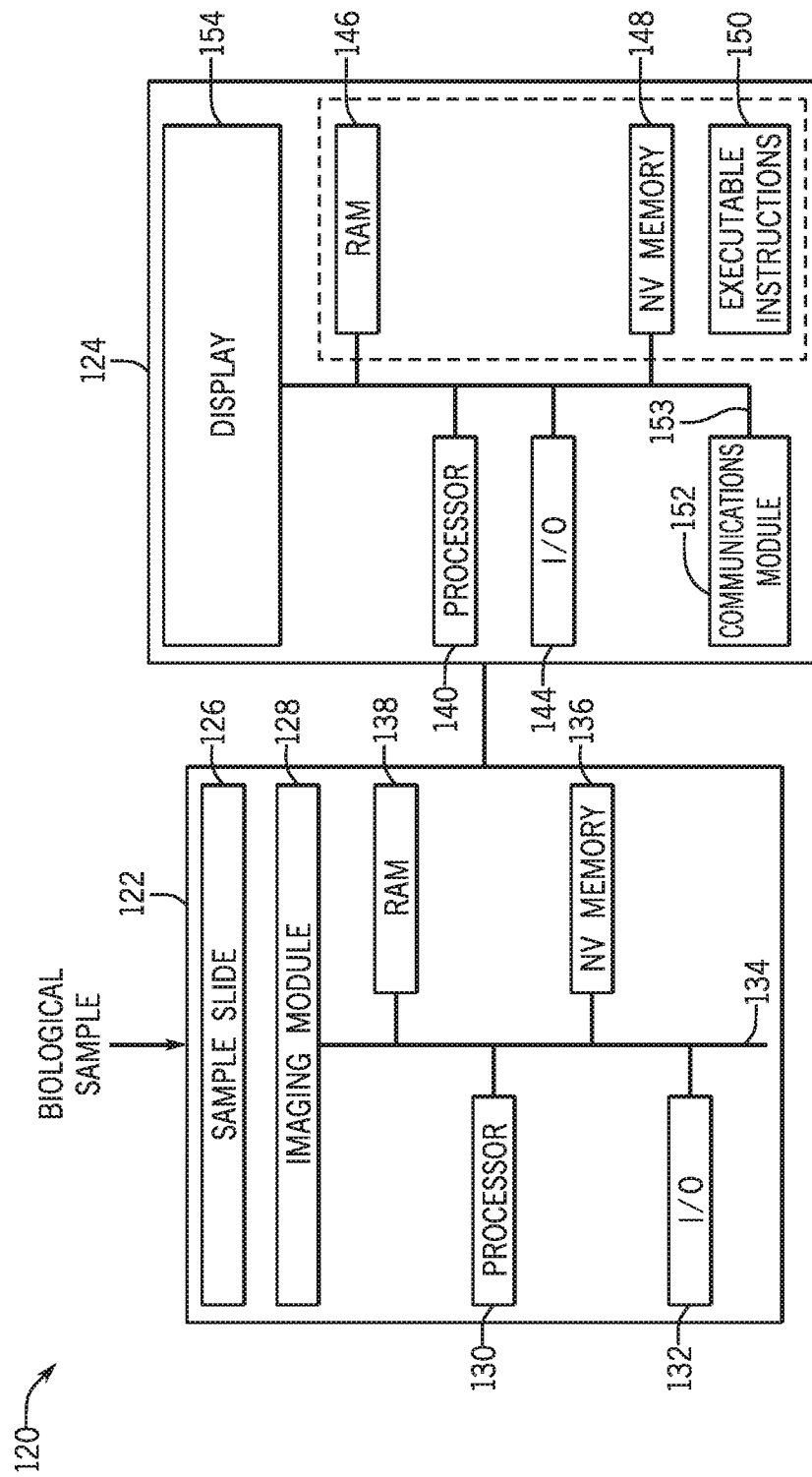
FIG. 20 is a block diagram of a sequencing device that may be used in conjunction with the embodiments of the disclosure.

The techniques disclosed herein may be implemented in conjunction with a sequencing device and/or a sequence analysis device. FIG. 20 is a schematic diagram of a sequencing device 120 that may be used, for example, to acquire and assess off-target reads that may be used in turn to design off-target hybridization probes. In another example, the sequencing device 120 may be used to acquire and assess sequencing data after using the off-target hybridization probes. The acquired sequencing data will have reduced off-target reads relative to a control that was not contacted with the off-target hybridization probes. The sequencing device 120 may be implemented according to any sequencing technique, such as those incorporating sequencing-by-synthesis methods described in U.S. Patent Publication Nos. 2007/0166705; 2006/0188901; 2006/0240439; 2006/0281109; 2005/0100900; U.S. Pat. No. 7,057,026; WO 05/065814; WO 06/064199; WO 07/010,251, the disclosures of which are incorporated herein by reference in their entireties. Alternatively, sequencing by ligation techniques may be used in the sequencing device 120. Such techniques use DNA ligase to incorporate oligonucleotides and identify the incorporation of such oligonucleotides and are described in U.S. Pat. Nos. 6,969,488; 6,172,218; and 6,306,597; the disclosures of which are incorporated herein by reference in their entireties. Some embodiments can utilize nanopore sequencing, whereby target nucleic acid strands, or nucleotides exonucleolytically removed from target nucleic acids, pass through a nanopore. As the target nucleic acids or nucleotides pass through the nanopore, each type of base can be identified by measuring fluctuations in the electrical conductance of the pore (U.S. Pat. No. 7,001,792; Soni & Meller, *Clin. Chem.* 53, 1996-2001 (2007); Healy, *Nanomed.* 2, 459-481 (2007); and Cockroft, et al. *J. Am. Chem. Soc.* 130, 818-820 (2008), the disclosures of which are incorporated herein by reference in their entireties). Yet other embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1, each of which is incorporated herein by reference in its entirety. Particular embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides, or with zero-mode waveguides as described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference in their entireties. Other suitable alternative techniques include, for example, fluorescent in situ sequencing (FISSEQ), and Massively Parallel Signature Sequencing (MPSS). In particular embodiments, the sequencing device 120 may be a HiSeq, MiSeq, or HiScanSQ from Illumina (La Jolla, Calif.).

In the depicted embodiment, the sequencing device 120 includes a separate sample processing device 122 and an associated sequence analysis device 124. Further, it is contemplated that the sequence analysis device 124 may be implemented separately form and not associated with the sample processing device 122. Accordingly, in such an embodiment, sequence analysis device 124 receives data from a remote sample processing device 122. However, these may be implemented as a single device. Further, the associated sequence analysis device 124 may be local to or networked with the sample processing device 122. In the depicted embodiment, the biological sample may be loaded into the sample processing device 122 as a sample slide 126 that is imaged to generate sequence data. For example, reagents that interact with the biological sample fluoresce at particular wavelengths in response to an excitation beam generated by an imaging module 128 and thereby return radiation for imaging. For instance, the fluorescent components may be generated by fluorescently tagged nucleic acids that hybridize to complementary molecules of the components or to fluorescently tagged nucleotides that are incorporated into an oligonucleotide using a polymerase. As will be appreciated by those skilled in the art, the wavelength at which the dyes of the sample are excited and the wavelength at which they fluoresce will depend upon the absorption and emission spectra of the specific dyes. Such returned radiation may propagate back through the directing optics. This retrobeam may generally be directed toward detection optics of the imaging module 128.

The imaging module detection optics may be based upon any suitable technology, and may be, for example, a charged coupled device (CCD) sensor that generates pixilated image data based upon photons impacting locations in the device. However, it will be understood that any of a variety of other detectors may also be used including, but not limited to, a detector array configured for time delay integration (TDI) operation, a complementary metal oxide semiconductor (CMOS) detector, an avalanche photodiode (APD) detector, a Geiger-mode photon counter, or any other suitable detector. TDI mode detection can be coupled with line scanning as described in U.S. Pat. No. 7,329,860, which is incorporated herein by reference. Other useful detectors are described, for example, in the references provided previously herein in the context of various nucleic acid sequencing methodologies.

The imaging module 128 may be under processor control, e.g., via a processor 130, and the sample preparation device 122 may also include I/O controls 132, an internal bus 134, non-volatile memory 136, RAM 138 and any other memory structure such that the memory is capable of storing executable instructions, and other suitable hardware components that may be similar to those described with regard to FIG. 20. Further, the associated sequence analysis device 124 may also include a processor 140, I/O controls 144, a communications module 152, and a memory architecture including RAM 146 and non-volatile memory 148, such that the memory architecture is capable of storing executable instructions 150. The hardware components may be linked by an internal bus 153, which may also link to the display 154. In embodiments in which the sequencing device 122 is implemented as an all-in-one device, certain redundant hardware elements may be eliminated.

The sequencing device 120 may be used to request target-specific hybridization probes. Further, the sequencing device 120 may be used to provide user inputs for off-target hybridization probe preparation. The user may provide inputs specifying a desired number of highest ranked sequences to be prepared as the set of off-target hybridization probes. The selections may alternatively or additionally be based on a desired percentage of off-target reduction.

Throughout this application various publications, patents and/or patent applications have been referenced. The disclosure of these publications in their entireties is hereby incorporated by reference in this application. The term comprising is intended herein to be open-ended, including not only the recited elements, but further encompassing any additional elements. While only certain features of the invention have been illustrated and described herein, many modifications and changes will occur to those skilled in the art. It is, therefore, to be understood that the appended claims are intended to cover all such modifications and changes as fall within the true spirit of the invention. Further, elements of the disclosed embodiments may be combined or exchanged. Accordingly, other embodiments are within the scope of the following claims.

What is claimed is:

1. A method of providing probes for off-target sequence capture in a targeted sequencing reaction, comprising:
    receiving a request for a set of target-specific hybridization probes;
    contacting the target-specific hybridization probes with a reference nucleic acid library generated from a reference sample, the reference nucleic acid library comprising a plurality of nucleic acid fragments, to generate a reference group of target-specific and off-target nucleic acid fragments bound to the target-specific hybridization probes, wherein the target-specific hybridization probes are generated based on the request;
    separating the reference group of nucleic acid fragments bound to the target-specific hybridization probes from unbound nucleic acid fragments;
    sequencing the reference group of nucleic acid fragments to generate reference sequencing data;
    identifying off-target sequences in the reference sequencing data; and
    providing a set of off-target hybridization probes based on the identified off-target sequences.

2. The method of claim 1, wherein providing the set of off-target hybridization probes based on the identified off-target sequences comprises ranking a prevalence of a plurality of off-target sequences in the reference sequencing data and selecting a plurality of highest prevalence off-target sequences to design the off-target hybridization probes such that the off-target hybridization probes are specific for the highest prevalence off-target sequences.

3. The method of claim 2, wherein selecting the plurality of highest prevalence off-target sequences comprises selecting a predetermined number of off-target sequences according to the ranking.

4. The method of claim 3, wherein the predetermined number is 5000 or fewer different off-target sequences.

5. The method of claim 4, wherein the target-specific hybridization probes are specific for 10,000 or more different target sequences.

6. The method of claim 2, wherein selecting the plurality of highest prevalence off-target sequences comprises selecting a subset of off-target sequences associated with at least 50% of off-target sequence reads in the reference sequencing data.

7. The method of claim 1, wherein providing the set of off-target hybridization probes based on the identified off-target sequences comprises identifying genomic locations corresponding to off-target sequences in the reference sample and selecting a plurality of off-target sequences associated with pre-determined genomic locations to design the off-target hybridization probes such that the off-target hybridization probes are specific for the pre-determined genomic locations.

8. The method of claim 7, wherein the pre-determined genomic locations are introns or intergenic locations.

9. The method of claim 1, comprising providing the set of target-specific hybridization probes.

10. The method of claim 1, comprising receiving a request to synthesize the set of target-specific hybridization probes and synthesizing the target-specific hybridization probes.

11. The method of claim 1, wherein the set of target-specific hybridization probes is a user-defined custom set of target-specific hybridization probes.

12. The method of claim 1, comprising providing an estimated reduction in sequencing cost associated with using the off-target hybridization probes with the reference sample, wherein the estimated reduction in sequencing cost is based on a reduction in off-target sequences.

* * * * *